United States Patent [19]

Kidwell

[11] Patent Number: 5,196,302
[45] Date of Patent: Mar. 23, 1993

[54] ENZYMATIC ASSAYS USING SUPERABSORBENT MATERIALS

[75] Inventor: David A. Kidwell, Alexandria, Va.

[73] Assignee: The United States of America as represented by the Sectetary of the Navy, Washington, D.C.

[21] Appl. No.: 574,175

[22] Filed: Aug. 29, 1990

[51] Int. Cl.$^5$ .................. C12Q 1/00; G01N 21/76; G01N 21/00

[52] U.S. Cl. .................. 435/4; 435/970; 422/52; 422/56; 422/57; 422/61; 422/82.65; 422/243

[58] Field of Search .................. 422/56, 57, 60, 61, 422/52, 82.05, 243; 435/970, 4

[56] References Cited

U.S. PATENT DOCUMENTS

| | | | |
|---|---|---|---|
| 3,926,736 | 12/1975 | Bucolo | 435/26 |
| 3,960,499 | 6/1976 | White | 422/55 |
| 4,273,870 | 6/1981 | Mollering et al. | 435/26 |
| 4,374,814 | 2/1983 | Gaylord | 423/245.1 |
| 4,391,904 | 7/1983 | Litman et al. | 435/7.91 |
| 4,613,569 | 9/1986 | Geisler et al. | 435/26 |
| 4,734,360 | 3/1988 | Phillips | 435/25 |
| 4,826,759 | 5/1989 | Guire et al. | 435/4 |

OTHER PUBLICATIONS

Curme, et al. "Multilayer Film Elements For Clinical Analysis: General Concepts" printed by Clin. Chem. in Rochester, N.Y., 1978 pp. 1335–1342.

Zuk et al., "Enzyme Immunchromatography–A Quantitative Immunoassay Requiring No Instrumentation" printed by Clin. Chem. in Palo Alto, Calif., 1985 pp. 1144–1150.

RAMP TM ProgetRINE TM Brochure printed in 1986.

"Enzyme Immunoassay" printed in Analyitcal Chemistry, vol. 56, No. 8 Jul. 1984.

RAMP TM Urine hCG Assay Brochure printed in 1986.

Granite Diagnostics, Inc. Pamphlet.

Grenner et al. "Multilayer Fluorescent Immunoassay Technique" printed in Clin. Chem. vol. 35 No. 9, 1989.

Kidwell "Superasorbent Polymers–Media for the Enzymtic Detection of Ethyl Alcohol in Urine" printed in Analytical Biochemistry 1989 pp. 257–261.

Primary Examiner—John W. Rollins
Attorney, Agent, or Firm—Thomas E. McDonnell; Barry A. Edelberg

[57] ABSTRACT

An apparatus for conducting a highly sensitive assay is provided wherein the level of a specific material is detected using a reaction which produces a detectable substance such as a colored dye or a fluorescent material in proportion to the concentration of the material being detected and which is carried out on an absorbent detecting layer comprising a superabsorbent polymeric material. The use of the superabsorbent polymeric materials greatly increases the sensitivity of the assay in a manner not achieved in the prior art because these polymeric materials are an excellent medium for the detection of the color changes caused by the reactants in the assays. These superabsorbent polymers offer increased sensitivity of up to about ten times greater than that which was possible using conventional backing materials as the absorbent layer in assays. The present invention comprises a quick, inexpensive, and accurate means for testing materials such as alcohol with a sensitivity that approaches 0.001% (w/v). A method of conducting colorimetric or other assays in accordance with the present invention is also provided. The present invention is especially useful in performing enzymatic assays.

14 Claims, 1 Drawing Sheet

ENZYMATIC ASSAYS USING SUPERABSORBENT MATERIALS

BACKGROUND OF THE INVENTION

1. Field of the Invention

The invention relates in general to an improved method and apparatus for carrying out colorimetric, fluorimetric or photometric enzymatic assays which employ absorbent materials. In particular, this invention relates to the use of a superabsorbent polymeric material as the absorbent detecting layer in enzymatic assays which employ an enzyme reaction to produce a change in the spectral properties of a particular substance which is detectable by means of a suitable detecting device in order to enhance the sensitivity and detecting capacity of the assay.

2. Description of the Prior Art

In the detection of small molecules such as drugs, environmental toxins, and other compounds, it is quite common to use slide technology which primarily employs competitive binding assays using an antibody and an enzyme-labelled drug. Depending upon the design of the assay, several wash steps are usually employed, after which the enzyme substrate is added. Most of these assays operate by the formation of a color after a period of time whose intensity varies depending on the concentration of the detected drug in the test fluid. Still other assays operate by assessing fluorescence or reactions producing chemical luminescence. With most of these assays, the color change or photoluminescence will develop in an absorbent detecting layer which is generally a paper medium such as blotter paper. Unfortunately, however, blotter paper and similar materials are disadvantageous because they are opaque and have a low water absorbing capacity. Since the detection layer is opaque and the color or light formed is distributed throughout the medium, not all of the signal can be observed. Further, a low absorption capacity also means that less test fluid can be used, and thus less of the analyte is available for analysis. As a result, commonly used absorbent paper materials reduce the sensitivity of these enzymatic assays.

Alternative slide technologies are available, but these have disadvantages as well. In the Ektachem dry reagent system (see Curme et al., *Clin. Chem.* 24(8): 1335-1342 (1978)), agarose is used instead of blotter paper in the detection layer. In this system, the slide consists of three layers: a spreading layer, a polymer layer, and a protective layer. The test fluid such as a serum sample is applied through the spreading layer and diffuses into the polymer layer wherein an enzymatic reaction produces a colored dye whose concentration is proportional to the glucose concentration in the test fluid. This system is disadvantageous because of the slow hydration of the agarose polymer which therefore requires a complex spreading layer for uniform fluid distribution.

Superabsorbent polymers are a class of materials that are unique with regard to their water absorbing abilities. These polymers can absorb up to at least about 2,000 times their weight in water. The use of superabsorbent polymers as the absorbent material in the detecting layer of the colorimetric or photometric assays referred to above would be highly advantageous because these polymers can become hydrated much more quickly, can form colorless and transparent gels, and require little or no control of the amount of fluid used because excess fluid (beyond that which is absorbed) will diffuse out of the reaction area and no color will be produced.

It is thus highly desirable to develop a system by which superabsorbent polymeric materials can be used to improve the sensitivity of competitive binding assays in which an absorbent detecting layer is used in a colorimetric or photometric enzymatic analysis.

SUMMARY OF THE INVENTION

In accordance with the present invention, an improved method and apparatus for conducting an enzymatic assay wherein an absorbent layer is used for the detection of a specific material is provided which comprises using superabsorbent polymeric materials in the absorbent layer. In the enzymatic assays of the present invention, a change in the spectral pattern of a substance or the production of fluorescence or luminescence is caused by the enzymatic reaction in an amount proportional to the concentration of the material being detected in the superabsorbent polymeric absorbent layer. Assays employing superabsorbent polymeric materials are vastly improved over prior systems employing blotter paper and other less suitable absorbent materials because the superabsorbent polymers become hydrated in less time, form colorless and clear gels, and require little or no control of the amount of fluid needed for the test. In addition, the gel formed from the superabsorbent materials is restrictive to fluid and molecular diffusion and therefore only the enzyme and substrate in the vicinity of the enzyme will react. The use of superabsorbent materials in accordance with the present invention will allow for increased sensitivity of at least from 2-10 times over those assays using conventional blotter materials.

The method and apparatus of the present invention will provide a quick, accurate, inexpensive, and highly sensitive test for a wide variety of materials that can be detected visually, spectroscopically, fluorimetrically, or in other ways. In one embodiment of the present invention, a colorimetric enzymatic assay for alcohol in body fluids can be carried out wherein sensitivity of the assay approaches about 0.001% (w/v).

BRIEF DESCRIPTION OF THE DRAWING FIGURES

DETAILED DESCRIPTION OF THE PRESENT INVENTION

Figure 1:
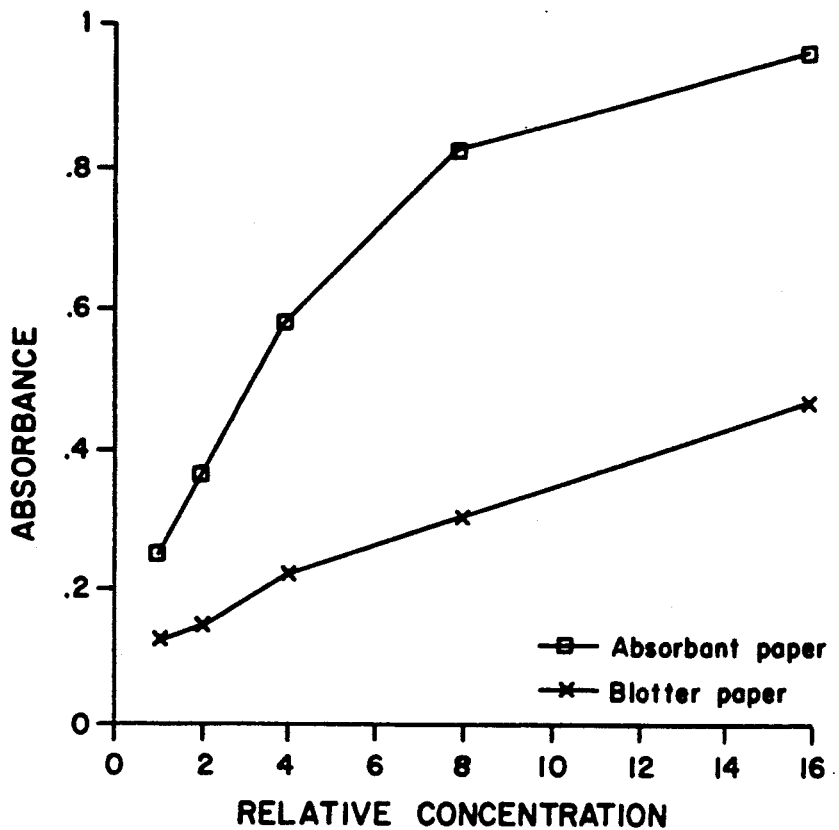
FIG. 1 is a graphic representation of reflected absorbence vs. concentration for the dye brilliant blue R used in an assay in accordance with the present invention.

According to the present invention, an improved enzymatic assay is provided wherein the concentration of a specific material is detected by a change in the spectral properties of a substance that develops on a superabsorbent detecting layer, or by the measurement of fluorescence or luminescence (including chemiluminescence, photoluminescence, etc.) produced in proportion to the concentration of the material to be detected. In the conventional enzymatic assay wherein a change in the spectral properties of a substance is monitored (herein a "colorimetric assay"), the concentration of a given material is determined using an enzymatic reaction which produces a colored dye (or dye which changes its spectral pattern at a non-visible wavelength) whose concentration is proportional to the concentration of the material to be detected. These assays are used for a wide variety of detectable materials including alcohol and glucose. In these assays, the color has been developed in an absorbent paper medium, most commonly blotter paper. In the present invention, the blotter paper is replaced by superabsorbent polymeric materials in order to greatly increase the sensitivity of the assay conducted on the material to be detected.

A number of superabsorbent polymeric materials are known and are suitable for use in the present invention. In the preferred embodiments, the superabsorbent polymers used will be capable of absorbing at least about 500 times their own weight in water. It is also preferred that the superabsorbent polymer be colorless and transparent and have an absorptive capacity for distilled water of at least about 200 mL/100 cm$^2$ (when coated onto a suitable backing material such as blotter paper or other conventionally used materials). Preferably, the superabsorbent polymer detecting layer will have an absorptive capacity of from about 200-500 mL/100 cm$^2$.

It is particularly preferred that the superabsorbent polymer to be used in the assays of the present invention consist of salts of polyacrylic acid or grafted acrylic acid on a starch backbone. These polymers can absorb up to at least 2,000 times their own weight in water. They are advantageous because they become hydrated in under 3 seconds, form a colorless and clear gel once hydrated, and need little or no control of the amount of fluid for each test because excess fluid will diffuse out of the reaction area and no color will be produced. Once formed, the gel is restrictive to fluid and molecular diffusion, and therefore only the enzyme and substrate in the vicinity of the enzyme will react. Diffusion of material from other areas is prevented. Particularly suitable for use in the present invention is the base hydrolyzed starch-polyacrylonitrile graft copolymer described in Weaver et al., *Die Starke* 29:413–422 (1977), incorporated herein by reference.

A further advantage is obtained because these polymers are weak acids and self-buffering around pH 7. This is advantageous because most enzymes of interest have maximal activity at or near a pH of about 7. Additionally, these polymers may be adjusted for other pH buffering ranges by the addition of the appropriate acid or base.

A number of other suitable superabsorbent materials which are widely known and readily available can be employed in the present invention. Such materials, which will absorb many times their own weight of fluid, include one type wherein particles or fibers may be described chemically as having a backbone of natural or synthetic polymers with hydrophilic groups or polymers containing hydrophilic groups being chemically bonded to the backbone or in intimate admixtures therewith. Included in this class of materials are such modified natural and regenerated polymers as polysaccharides including, for example, cellulose and starch and regenerated cellulose which are modified by being carboxyalkylated, phosphonoalkylated, sulphoalkylated or phosphorylated to render them highly hydrophilic. Such modified polymers may also be cross-linked to improve their water-insolubility. These same polysaccharides may also serve, for example, as the backbone onto which other polymer moieties may be bonded by graft copolymerization techniques. Such grafted polysaccharides and their method of manufacture are described in U.S. Pat. No. 4,105,033 (Chatterjee et al), incorporated herein by reference. These polysaccharide chains have grafted thereon a hydrophilic chain such as hydrolyzed polyacrylonitrile chains and copolymers of polyacrylamide and polysodium acrylate.

In addition to modified natural and regenerated polymers, the superabsorbent polymers may include hydrocolloid particle components comprising wholly synthetic hydrophilic particles. Examples of these components are polyacrylonitrile fibers which may be modified by grafting moieties thereon such as polyvinyl alcohol chains, polyvinyl alcohol itself, hydrophilic polyurethane, poly(alkylphosphonates), partially hydrolyzed polyacrylamides (e.g., poly(N-N-dimethyl acrylamide), sulphonated polystyrene, or a class of poly(alkylene oxide), such as described in U.S. Pat. No. 4,559,050 (Iskra), incorporated herein by reference. These highly hydrophilic synthetic polymers may be modified by other chemical treatments such as cross-linking or hydrolysis. Other suitable compounds include the nonionic hydrophilic polymers such as polyoxyethylene, polyoxypropylene and mixtures thereof which have been suitably cross-linked, either chemically or by irradiation. Still another more recent type of superabsorbent component suitable for use in the present invention is a derivative of isobutylene-maleic anhydride copolymer.

The superabsorbent materials employed in the present invention can be used along with blotter paper or other suitable backing material to provide a substrate for the various colorimetric or fluorimetric or photometric enzymatic assays which require absorbent materials. By suitable backing material is meant any appropriate rigid or semi-rigid surface layer used to provide a backdrop so that the color change, fluorescence, or luminescence can be more easily determined. Generally, these backing materials will include paper, such as blotter paper, and polymeric materials such as polyethylene, Teflon, or other plastics which can provide a white or reflective surface. Most preferably, the superabsorbent material used for spot tests is formed into an assembly consisting of one layer of blotter paper or other suitable backing material, a layer of superabsorbent polymer, and a protective layer comprised of air-laid tissue or other suitable thin protective material. By using paper as the background material, a white or reflective background is provided by which one can observe the spectral change. In this preferred assembly, the polymer layer provides the reaction medium, and the protective layer protects the polymer from damage during handling.

One suitable type of paper that has been impregnated with a superabsorbent polymer and used successfully in the apparatus of the present invention is manufactured by Grain Processing Corp. (Muscatine, Iowa) under the trade name WATER LOCK. ® It is available in several forms and is inexpensive, less than about ten cents per square foot. Particularly suitable is WATER LOCK ® L413, a laminated paper impregnated with 1 g/100 cm$^2$ of superabsorbent polymer which has an absorptive capacity for distilled water of approximately 225 mL/100 cm$^2$. As disclosed in Kidwell, *Anal. Biochem.* 182:257–261 (1989), incorporated herein by reference, laminate L415 (1.3 g/100 cm$^2$ superabsorbent polymer and 425 mL/100 cm$^2$ absorptive capacity) was also tested, and is less suitable for use in the invention.

The enzymatic assays employing superabsorbent polymeric materials in accordance with the present invention can be carried out using a wide range of detectable materials, dyes, and enzymes. Included in the invention would be those colorimetric assays wherein a dye is changed in color to give a visual indication of the spectral change in proportion to the concentration of material being detected, assays where change is recorded by devices sensing non-visible wavelengths of radiation, and assays where a fluorimetric or photometric analysis is carried out to assess concentration of a material by means of the observed fluorescence or luminescence. In all of these cases, the assays would be improved through the use of superabsorbent materials in an absorbent detecting layer.

As an example of the present invention, assays using superabsorbent materials have been used to determine the concentration of alcohol in a urine sample with a far greater sensitivity than previously used commercial assays. In this test for alcohol, the oxidation of alcohol by the enzyme alcohol dehydrogenase (AD) was used in a colorimetric assay to determine alcohol concentration. Alcohol dehydrogenase is highly specific for alcohol and would have no other interferences that would be found in normal human urine. Alcohol dehydrogenase requires NAD as a co-factor. NAD is reduced by alcohol dehydrogenase in the presence of alcohol to NADH. The NADH reduces a reagent such as phenazine methosulfate which in turn reduces a colorless tetrazolium salt to a highly colored formazan dye. This reaction cascade produces one molecule of formazan dye for each molecule of alcohol oxidized. The quantity of alcohol can then be determined down to a very finite amount by comparing the intensity of the spot produced with the known standards. The general scheme of this reaction is as follows:

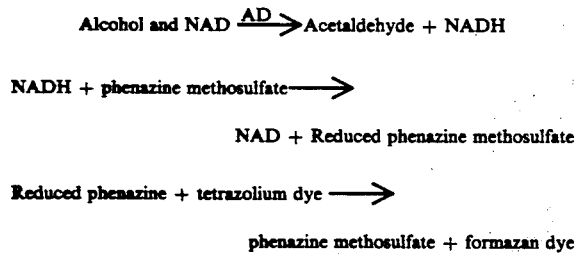

Through the use of the superabsorbent-paper assembly as the absorbent detecting layer in this colorimetric enzymatic assay, the detection of alcohol was accomplished with the sensitivity approaching 0.001% (w/v). Alcohol levels in 500 random urine samples were determined and the levels ranged from 0.06 to less than 0.001%, with the majority of positives being near 0.005%. Previously used colorimetric assays without superabsorbent materials have not allowed detection of alcohol levels below about 0.01%. Other problems are also avoided in that the color formed with blotter paper as a matrix would have been less distinct without the superabsorbent materials. Additionally, when blotter paper alone is employed, the volume of urine used must be reduced which results in much lower amounts of alcohol to be detected, and thus much lower sensitivity.

Alternatively, chemical reactions that employ a coupled-enzyme system using alcohol oxidase and horseradish peroxidase have also been employed in commercial alcohol dip stick tests such as the "Alcoscan" by Lifescan, Inc. of Mountainview, Cal. In these tests, the alcohol oxidase generates hydrogen peroxide from alcohol and the horseradish peroxidase oxidizes dye with the hydrogen peroxide to form a colored spot. These colorimetric enzyme assays could also be improved through the use of superabsorbent polymeric materials in accordance with the present invention.

In general, the present invention provides a method of improving the sensitivity of enzymatic colorimetric analyses by use of superabsorbent polymeric materials as the absorbent detecting layers in those assays. The invention can be utilized in the form of a test kit which will include the enzymes for the reaction and test strips containing the superabsorbent polymers. The use of the present invention will provide a quick, inexpensive, readily diagnosable colorimetric test for materials such as alcohol, cholesterol, alkaline phosphatases or glucose in blood, urine, or other bodily samples. In addition, the invention is suitable for use in a wide variety of other enzymatic assays, including immunoassays and other procedures wherein chromatographic or chemiluminscent assays are carried out using absorbent materials (see, e.g., Zuk et al., *Clin. Chem.* 31(7):1144–1150 (1985)).

The scope of the present invention is defined in the appended claims, and the following examples are only presented as illustrative of the present invention:

MATERIALS AND EQUIPMENT USED IN THE EXAMPLES

For colorimetric assays performed in accordance with the present invention, paper impregnated with a superabsorbent polymer such as a polyacrylic acid with a salt such as sodium or potassium either alone or copolymerized with other acrylic acids such as polymethacrylic acid was used in the present invention. The paper was manufactured by Grin Processing Corp. of Muscatine, Iowa under the trade name WATER LOCK ®. The tests were performed with WATER LOCK ® L413 laminated paper as the medium. This paper has 1 g/100 cm$^2$ of super absorbent polymer with an absorptive capacity for distilled water of approximately 225 mL/100 cm$^2$. Blotter paper was purchased from Schleicher and Schuell and the other reagents from Sigma. For comparison purposes of the test, the super absorbent paper and the blotter paper were glued to a glass substrate and the reflected, optical absorbencies of the spots tested were read on a Shimadzu CS-930 Dual-Wavelength TLC Scanner at 585 nm.

EXAMPLE 1

Comparison of Blotter Paper and Superabsorbent Polymer

Figure 2:
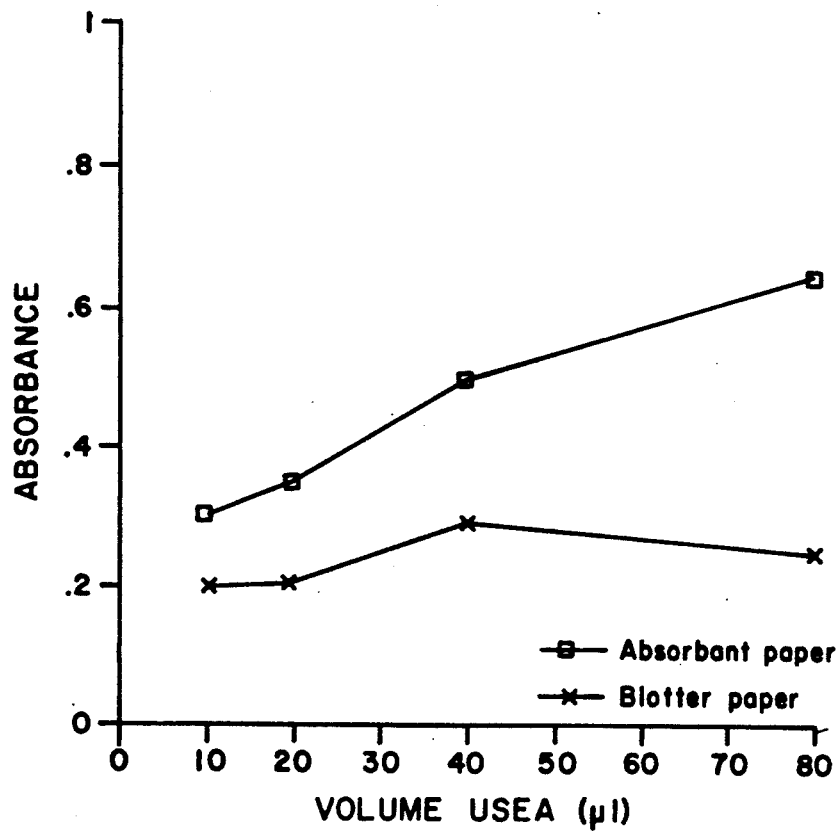
FIG. 2 is a graphic representation of reflected absorbance vs. volume at a constant concentration for the dye brilliant blue R used in an assay in accordance with the present invention.

FIG. 1 shows the average optical absorbance in the center of the spot where a solution of brilliant blue R was spotted on both blotter paper and L413 superabsorbent paper at different concentrations. In all cases the optical absorbance of the spot on the superabsorbent paper was about twice that of the spot on blotter paper. In FIG. 2, the volume of the solution spotted was increased while keeping the concentration of the dye constant. Since the solution spreads on blotter paper, the absorbance at the center stays relatively constant with increasing volume. However, superabsorbent paper has a much higher capacity for water, and the dye solution can be concentrated in a smaller area. Therefore, the intensity of the spot increases with the amount of dye solution used until the capacity of the superabsorbent paper is exceeded. Both of these figures taken together indicate that a superabsorbent paper would be expected to have a minimum of twice the sensitivity of blotter paper for low solution volumes and 4-10 times more sensitivity for larger volumes of solution.

EXAMPLE 2

Strip Preparation and Test

Test of the assays of the present invention were performed on urine samples and includes pH capacity, red and blue dye coloration, and a test for an ascorbic acid interference. Four spots were applied in a column with twenty columns/9×30-cm sheet of paper. One spot contained all the detection reagents using 3-(4, 5-dimethylthiazol-2-yl)-2, 5-diphenoltetrazolium bromide (MTT, a blue formazan dye); the second spot contained all the reagents using p-iodonitrotetrazolium violet (INT, a red formazan dye); the third spot contained only MTT, phenazine methosulfate, and buffer (to test for the presence of ascorbic acid); and the fourth spot contained buffer and cresol red (to test for pH).

Strips were prepared immediately before use. A solution consisting of 400 μl of NAD (8 mg/mL in 0.5 m phosphate buffer, pH 8.0), 100 μl tetrazolium dye (2 mg/mL in water), 100 μl alcohol dehydrogenase (Ec 1.1.1.1) (1 mg/mL, 300 units/mg, phosphate buffer), and 40 μl phenazine methosulfate (1 mg/mL, water) were used. Copper sulfate (0.5 mg/mL, 20 μl) was also added in some preparations. In the test for the presence of ascorbic acid, the NAD and alcohol dehydrogenase were replaced by buffer. The pH test used 0.1% cresol red in buffer. The spots were applied simultaneously to the super absorbent polymer materials and the blotter paper with a Titertek Multi-Channel Pipetter, applying 8 μl/spot, 4 spots per column.

Urine was tested by spotting one drop on each of the four spots per column using a disposable pasture pipette. After the whole sheet was spotted, it was set aside for five-ten minutes, after which the intensity of the ascorbic acid test spot was examined. If it was a darker blue than other spots in different columns, that urine sample was considered to have an ascorbic acid interference. Approximately 15 out of the 500 urine samples tested showed an ascorbic acid interference so severe as to obscure the presence or absence of alcohol. If the urine sample had no ascorbic acid interference, that spot was compared to the spot containing the enzyme. If the spot containing the enzyme was darker, that urine sample was considered positive for alcohol. Approximately 300 urine samples could be screened per hour using two people.

The 0.5M phosphate buffer had sufficient buffering capacity to prevent the pH from rising above 8.5 and inhibiting the enzyme. If the pH was above this level, the cresol red would produce a red color. Only one sample had any indication of being above this pH level. To adjust the range of detection of alcohol, several different formulations were tried varying the concentration of copper sulfate. Initially, it was desired to examine only samples having high levels of alcohol (>0.05%). To decrease the sensitivity of the test, therefore, copper sulfate was used in approximately 100 of the 500 samples tested to inhibit color development. Since many of the samples did not have appreciable amounts of alcohol, the use of copper sulfate was discontinued. Approximately 50 positive samples were found in the survey to have varying levels of alcohol above the detection limit of 0.001% (w/v).

GC/MS confirmation of the above tests were performed on each positive sample with a Hewlett-Packard 5970 mass spectrometer interfaced to a Hewlett-Packard 5890 GC. A 30 m×0.25 mm RSL200 (Alltech Associates, Inc.) capillary GC column was used. The column was operated isothermally at 35° C. using helium as the carrier gas at a column head pressure of 5 psi. The retention time for the ethyl alcohol peak was 1.6 min.

The alcohol level in urine is related to the blood alcohol level. However, for accurate results, the urine sample must be collected by voiding the bladder, waiting 30 minutes, and then obtaining the sample. If random urine samples are obtained, they reflect average alcohol levels and liquid intake. The test used for alcohol is based on an assay developed for the detection of NAD (see Bernofsky et al, *Anal. Biochem.*, 53:452-458 (1973)) which relies on the oxidation of alcohol by the enzyme alcohol dehydrogenase (AD). In this assay, NAD is reduced by alcohol dehydrogenase in the presence of alcohol to NADH. The NADH so produced produces phenazine methosulfate which in turn reduces a colorless tetrazolium salt to a high colored formazan dye. The quantity of alcohol can be determined by comparing the intensity of the spot produced with known standards. Potential interferences for this detection scheme, including pH, heavy metals, and ascorbic acid, are indicated at Table 1. These interferences are characteristic of the enzyme system employed and are unrelated to the use of a superabsorbent matrix in accordance with the present invention.

Tests indicated the detection of alcohol levels in amounts as low as 0.001% (w/v). Of the fifty samples that were detected as positive, thirty were retained for confirmation of the alcohol levels by GC/MS. These results are given in Table 2. Two samples were detected in this survey with alcohol levels of greater than 0.4% which were both blind quality control samples inserted at the laboratory. Several other quality control samples with lower alcohol levels were also detected and removed from the results shown in Table 2 leaving a total of 26 samples.

Without the use of a superabsorbent paper, the detection of alcohol levels below 0.01% would have been impossible. The color formed with blotter paper as a matrix would have been less distinct. Also, the urine volume must be reduced when blotter paper is employed which results in lower amounts of alcohol and therefore lower sensitivity. In the test of the present invention, the quick spot test for alcohol developed for use along with the superabsorbent paper will preferably employ a blue spot for the evaluation. Interferences by ascorbic acid are not so common as to warrant their elimination if this test is to be used for survey purposes. Smaller amounts of ascorbic acid may be compensated for by using a control spot. Needed buffering capacity must still be established and optimized, however, with 0.5M phosphate at pH 8.0, the test performed satisfactorily. Alcohol levels in these random samples ranged in value from 0.006 to less than 0.001%, with the majority of positives being near 0.005%.

TABLE 1

| Material | Spot Test Interferences Effect |
|---|---|
| pH | Inhibits enzyme |

TABLE 1-continued

| Spot Test Interferences | |
|---|---|
| Material | Effect |
| Heavy Metals (Ag, Cu, Fe, Hg) | Inhibits enzyme or oxidizes NADH produced |
| Ascorbic acid | Positive interference - reduces dye |

TABLE 2

Urine Alcohol Levels in Positive Samples as Confirmed by GC/MS

| % Alcohol Concentration | Number of Positives |
|---|---|
| 0.001–0.003 | 6 |
| 0.003–0.007 | 10 |
| 0.007–0.01 | 3 |
| 0.01–0.02 | 3 |
| 0.02–0.05 | 3 |
| >0.05 | 1 |

Obviously, many modifications and variations of the present invention are possible in light of the above teachings. It is therefore to be understood that, within the scope of the appended claims, the invention may be practiced otherwise than as specifically described.

What is claimed is:

1. In an apparatus for conducting an assay which includes an absorbent detecting layer and wherein the concentration of a specific material is determined through the use of a reaction which takes place on the absorbent detecting layer and which produces a detectable substance whose concentration is proportional to the concentration of the specific material being assayed, the improvement wherein the absorbent detecting layer forms a colorless and transparent gel upon hydration, has an absorptive capacity for distilled water of at least about 225 mL/g and is a polymeric material which hydrates in under 3 seconds.

2. An assay apparatus according to claim 1 wherein the polymeric material comprises a polymethacrylic acid salt.

3. An assay apparatus according to claim 1 wherein the polymeric material comprises a salt of an acrylic acid grafted onto a starch backbone.

4. An assay apparatus according to claim 1 wherein the polymeric material comprises a base-hydrolyzed starch-polyacrylonitrile graft copolymer.

5. An assay apparatus according to claim 1 wherein the polymeric material comprises a polyacrylonitrile fiber modified by grafting thereon a polyvinyl alcohol chain or a polyacrylamides.

6. An assay apparatus according to claim 1 wherein the polymeric material is coated onto a backing material.

7. An assay apparatus according to claim 6 wherein the backing material comprises paper.

8. An assay apparatus according to claim 6 wherein the backing material is coated by approximately 1 g/100 cm$^2$ of said polymeric material.

9. An enzymatic assay apparatus according to claim 1 wherein the polymeric material is capable of absorbing at least about 500 times its own weight in water.

10. In a method of conducting an assay wherein the presence of a specific material is determined through the use of a reaction which takes place on an absorbent detecting layer and which produces a detectable substance whose concentration is proportional to the concentration of the specific material being assayed, the improvement wherein the absorbent detecting layer forms a colorless and transparent gel upon hydration, has an absorptive capacity for distilled water of at least about 225 mL/g and is a polymeric material which hydrates in under 3 seconds.

11. A method of conducting a highly sensitive enzymatic assay comprising the steps of:
   a) providing an absorbent detecting layer having an absorptive capacity for distilled water of at least about 225 mL/g and made from a polymeric material which hydrates in under 3 seconds, said absorbent detecting layer forming a colorless and transparent gel upon hydration;
   b) adding an enzyme-containing set of reagents capable of reacting in the presence of a specific material so as to produce, in said polymeric material, a detectable substance in an amount dependent upon the concentration of the specific material present in the assay;
   c) adding a fluid suspected of containing the specific material to be assayed in a concentration ranging from 0% to 100% so that a detectable substance is produced from the set of reagents in an amount dependent upon the concentration of the specific material added to the reagents; and
   d) determining the presence in said fluid of the specific material being assayed by detecting the presence of the detectable substance present in said polymeric material following the enzymatic reaction.

12. The method of claim 11, wherein step d comprises the step of determining the concentration of the specific material being assayed by determining the amount of the detectable substance present following the enzymatic reaction which is dependent upon the concentration of the specific material being assayed.

13. A test kit for performing an enzymatic assay wherein the concentration of a specific material is determined through the use of an enzyme reaction which takes place on absorbent detecting layer having an absorptive capacity for distilled water of at least about 225 mL/g, and made from a polymeric material which hydrates in under 3 seconds, and which produces a detectable substance in an amount dependent upon the concentration of the specific material being assayed comprising a test strip having a layer of said polymeric material, and an enzyme-containing set of reagents capable of reacting in the presence of the specific material being assayed to produce, in said layer of polymeric material, a detectable substance in an amount dependent upon the concentration of the specific material being assayed, said absorbent detecting layer forming a colorless and transparent gel upon hydration.

14. An assay apparatus according to claim 1, wherein the absorbent detecting layer has an absorptive capacity of at least about 200 ml/100 cm$^2$.

* * * * *